US008911705B2

(12) United States Patent
Ziabreva et al.

(10) Patent No.: US 8,911,705 B2
(45) Date of Patent: Dec. 16, 2014

(54) DIAGNOSTIC SUBSTANCE AND METHOD FOR THE ANALYSIS OF METABOLISM PROCESSES IN THE BRAIN

(75) Inventors: Iryna Ziabreva, Wardley Gateshead (GB); Petra Henrich-Noack, Beaumont (IE); Juergen Goldschmidt, Magdeburg (DE); Kathrin Baldauf, Magdeburg (DE); Henning Scheich, Samswegen (DE); Klaus G. Reymann, Niederndodeleben (DE); Ulrich H. Schroeder, Eussenheim (DE); Claudia Pforte, Schochwitz (DE); Monika Riek-Burchardt, Kloster Neuendorf (DE)

(73) Assignee: Leibniz-Institut fuer Neurobiologie Stiftung des Oeffentlichen Rechts, Magdeburg (DE)

( * ) Notice: Subject to any disclaimer, the term of this patent is extended or adjusted under 35 U.S.C. 154(b) by 778 days.

(21) Appl. No.: 12/087,275

(22) PCT Filed: Dec. 29, 2006

(86) PCT No.: PCT/DE2006/002345
§ 371 (c)(1),
(2), (4) Date: Feb. 26, 2009

(87) PCT Pub. No.: WO2007/076848
PCT Pub. Date: Jul. 12, 2007

(65) Prior Publication Data
US 2009/0317325 A1  Dec. 24, 2009

(30) Foreign Application Priority Data
Dec. 30, 2005  (DE) .......................... 10 2005 063 174

(51) Int. Cl.
*A61K 51/00*  (2006.01)
*A61M 36/14*  (2006.01)
*A61K 49/00*  (2006.01)
*A61K 49/10*  (2006.01)
*A61K 51/04*  (2006.01)

(52) U.S. Cl.
CPC ........... *A61K 49/0002* (2013.01); *A61K 49/103* (2013.01); *A61K 51/0476* (2013.01); *A61K 51/0478* (2013.01)
USPC ........................... 424/1.11; 424/1.61; 424/9.1

(58) Field of Classification Search
CPC ........... A61K 51/0478; A61K 49/0002; A61K 51/0476; A61K 49/103
See application file for complete search history.

(56) References Cited

PUBLICATIONS van Royen, E. A. de Bruine, J. F.; Hill, Th. C.; Vyth, A.; Limburg, M.; Byse, B. L.;O'Leary, D. H.; de Jong, J. M. B. V.; Hijdra, A.; van der Schoot, J. B. Cerbral blood flow imaging with thallium-201 diethyldithiocarbamate. J. Nucl. Med. 1987, 28, 178-183.*
Blau et al. Semin. Nucl. Med. 1985, 15, 329-334.*
Grisham et al. J. Biol. Chem. 1974, 249, 6738-6744.*
De Bruine et al., "Thallium-201 Diethyldithiocarbamate: An Alternative to Iodine-123 N-Isopropyl-p-Iodoamphetamine," J Nucl Med, 26:925-30 (1985).
Lear et al., "Autoradiographic Comparison of Thallium-201 Diethyldithiocarbamate, Isopropyliodoamphetamine and Iodoantipyrine as Cerebral Blood Flow Tracers," J Nucl Med, 28:481-6 (1987).
Ballinger et al., "Technetium-99m Diethyldithiocarbamate (DDC): Comparison with Thallium-201 DDC as an Agent for Brain Imaging," Appl. Radiat. Isot., 38(8):665-8 (1987).
Limburg et al., "Single-Photon Emission Computed Tomography and Early Death in Acute Ischemic Stroke," Stroke, 21:1150-5 (1990).
Scopinaro et al., "Encephalic Uptake of Thallium-201-Labeled Diethyldithiocarbamate (DDC)," Eur J Nucl Med, 15(8):575 (1989).
Verhoeff et al., "A Comparison of Thallium-201-Labeled DDC and Technetium-99m-Labeled HMPAO SPECT and CT in Patients with a Cerebrovascular Accident," Eur J Nucl Med, 16(7):559 (1990).
Limburg et al., rCBF-SPECT in Brain Infarction: When Does It Predict Outcome? J Nucl Med, 32:382-7 (1991).
De Bruine et al., "SPET brain imaging with 201 diethyldithiocarbamate in acute ischaemic stroke," Eur J Nucl Med, 17:248-51 (1990).
Overby et al., "Effect of Blood-Brain Barrier Disruption on Thallium-201 Diethyldithiocarbamate Distribution in Rat Brains," J Nucl Med, 27:736 (1986).
Goldschmidt et al., "High-resolution mapping of neuronal activity by thallium autometallography," NeuroImage, 23:638-47 (2004).
Blau, "Radiotracers for Functional Brain Imaging," Seminars in Nuclear Medicine, vol. XV, No. 4, pp. 329-334 (1985).

* cited by examiner

*Primary Examiner* — Michael G Hartley
*Assistant Examiner* — Sean R Donohue
(74) *Attorney, Agent, or Firm* — Kriegsman & Kriegsman

(57) ABSTRACT

The present invention relates to a diagnostic substance, containing at least one complex of lipophilic anions and metal ions, wherein the lipophilic anions are selected from the group comprising: triethylene tetramine dihydrochloride (TETA), ethyl cysteinate dimer (ECD), methoxyisobutyl-isonitrile (MIBI), HMPAO (d,l-hexamethylpropylene aminoxime), ethylenediamine N,N,N',N'-tetraacetanilide (ED-TAN), dimethyldithiocarbamate (DMC) and diethyldithiocarbamate (DDC) and glycine N,N'-[1,2-ethanediylbis(oxy-2,1-phenylene)]bis [N-(carboxymethyl)-1,1'-bis[2-(octadecyloxy)ethyl]ester (DP-109), and wherein the metal ions are selected from the group comprising thallium isotopes, lead isotopes, cobalt isotopes and manganese isotopes, together with solvents, adjuvants and/or vehicles. The diagnostic substance is used for investigating metabolic processes in the brain and/or central nervous system (CNS).

2 Claims, 2 Drawing Sheets

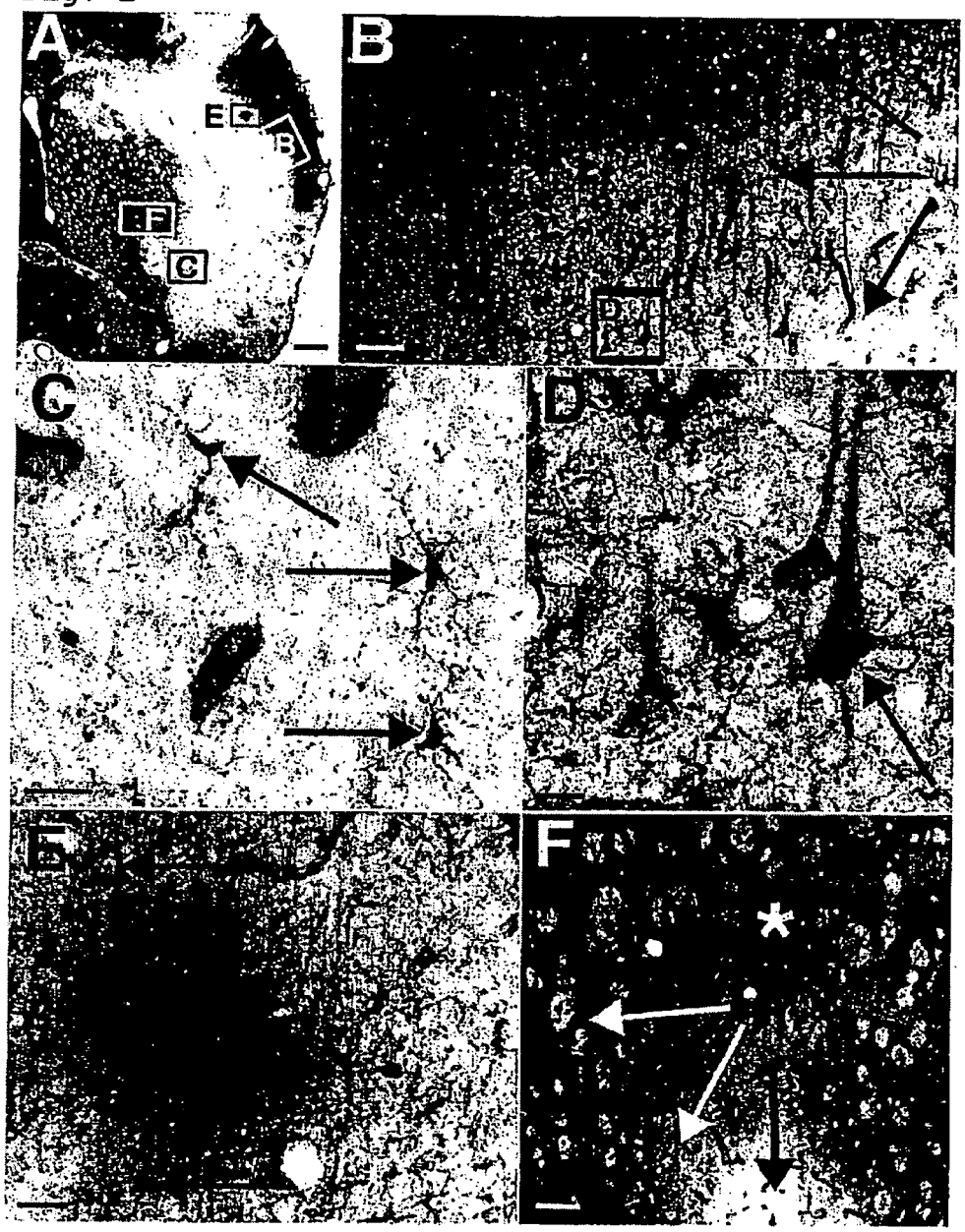

DIAGNOSTIC SUBSTANCE AND METHOD FOR THE ANALYSIS OF METABOLISM PROCESSES IN THE BRAIN

BACKGROUND OF THE INVENTION

The present invention relates to a diagnostic substance which contains at least one complex of lipophilic anions and metal ions, as well as the use of the diagnostic substance for investigating metabolic processes in the brain and/or central nervous system (CNS).

Changes in the activity and metabolism of neurons and glial cells are accompanied by changes in the rate of uptake and the intracellular and extracellular concentrations of numerous cations (e.g., Na+, K+, Ca++, Mg++, Zn++). In pathological processes, particularly ischemia, tumors, inflammations and neurodegenerative disorders (dementias, Alzheimer's disease), there is altered neuronal and glial cell activity and shifts in cation equilibria occur. In addition and particularly in the case of degenerative changes, tissue components have an altered cation binding behavior.

Changes in cation metabolism in the CNS could previously not be investigated in routine diagnosis.

Attempts to investigate cation metabolism by means of nuclear resonance spectroscopy are known, wherein a prerequisite is that measurable isotopes are present. This condition is in fact fulfilled in the case of the measurement of potassium ions, but the three-dimensional resolution obtained in these investigations is usually poorer than in the case of isotope investigations by means of a gamma camera. And in the case of other isotopes, such as calcium, for example, an investigation is generally not possible by means of NMR spectroscopy.

Paramagnetic manganese (Mn++) can only be used as a tracer for calcium metabolism in animal experiments—after opening the blood-brain barrier. A transfer of this method to humans, however, has previously not been possible, since the channeling of non-toxic quantities of manganese through the blood-brain barrier and utilizing imaging for magnetic resonance in humans has not as yet been successful.

The single method that could be used up to now for the direct measurement of metabolic changes in the CNS is the positron emission tomographic measurement of glucose metabolism ($^{18}$fluorine-deoxyglucose PET).

Due to the high cost of the equipment, however, this method is utilized only at a few selected clinics and it can be transferred only with difficulty to the arena of the physician's practice.

Today, the changes in ion metabolism are usually indirectly investigated, for example, via changes in the mobility of water molecules in magnetic resonance tomography (MRT) or via cerebral blood flow measurements.

Complexing agents which complex the isotopes of specific heavy-metal ions are utilized, among others, for the so-called tracer technique. The heavy-metal ion bound in these complexes only plays the role of a "reporter", which will indicate where the complexed compound diffuses in the body. The actual diagnostic substance is the complexed compound.

It is a disadvantage in this indirect measurement, however, that the consequential changes that follow disrupted metabolism—such as altered blood flow or an altered resonance behavior that can be measured by means of magnetic resonance—are measured exclusively. And as yet it can only be estimated as to how and under what conditions disruptions in cellular metabolism lead to changes in blood flow or alterations of water proton resonance.

A direct measurement of cation metabolism, in contrast, has the advantage that a direct view into cellular metabolism is offered. In therapy monitoring, the direct determination of cation metabolism could be even more important than for simply establishing a diagnosis of a CNS disorder, since it is still not clear how the recovery of metabolism affects the above-named consequential changes (blood flow, water proton resonance). For this reason, it is completely conceivable that cellular metabolism recovers without a change in the indirect water signals that can be measured with magnetic resonance or that changes occur before recovery.

In the case of the above-mentioned indirect method for investigating ion metabolism, the selection of a suitable tracer is of the utmost importance.

Here, one of the most important criteria in the selection of the complexing agent and the metal ion to be complexed in this method is the stability of the complexed compound in a physiological environment. This is because only an intact tracer in which the metal ion is still bound to the complexing agent, makes possible the above-described detection of the complexing agent with methods in which metal ions are detected.

In this context, the following are known, for example: the use of the non-radioactive isotopes of thallium and of the gamma radiator $^{201}$Tl, the use of the non-radioactive isotopes of cobalt, and of the gamma radiator $^{57}$Co and the positron emitter $^{55}$Co, the non-radioactive isotopes of manganese and the positron emitter $^{52}$mMn, as well as the non-radioactive isotopes of lead, iron and nickel.

The tracer, and to be more precise, the reporter in the tracer, is then detected for paramagnetic isotopes (manganese, cobalt, iron) by means of nuclear magnetic resonance methods, [or] positron emission tomography, PET, for the detection of positron emitters and single-photon emission tomography, SPET, for the detection of gamma radiators.

This stability of the tracer molecules, which brings about the circumstance that almost no free metal ions are retained in the investigated tissue, nevertheless requires that imaging detection methods are sufficiently rapid in order to produce an image in the period of time in which the tracer is found in the region of investigation. In a study by Ballinger et al., Appl. Radiat. Isotop. Vol. 38, No. 8, pages 665-668, 1987, this problem was discussed precisely in connection with SPECT investigations with a gamma camera in the measurement of cerebral blood flow. Since the gamma camera at that point in time required 20 to 40 minutes in order to accumulate an image, the suitability of two tracer molecules was discussed for this method. A comparison was made between two lipophilic complexes, i.e., technetium-99m-diethyldithiocarbamate ($^{99m}$Tc-DDC) und thallium-201 diethyldithiocarbamate ($^{201}$Tl-DDC). Both substances were investigated as to whether they were suitable for the imaging method utilized for blood flow measurements in the brain.

In this way it was established that both complexed compounds show a good cerebral uptake due to their lipophilic nature, but have very different retentions. This difference in retention was explained by the fact that $^{201}$Tl-DDC decomposes spontaneously in the brain and ionic $^{201}$Tl is formed, which cannot cross the blood-brain barrier. In contrast, $^{99}$mTc-DDC has an essentially lower rate of decomposition in the brain, for which reason, the compound is retained there to a lesser extent.

In spite of this knowledge, it was estimated that $^{201}$Tl-DDC was less suitable in the described method among others, since it is not optimally suitable for the SPECT method due to its gamma emission. In addition, it was established that $^{201}$thallium is disadvantageous due to its half-life of three days.

No instance has previously been known, however, in which the decomposition of a metal chelate complex in a physiological environment has been utilized in a targeted manner for diagnosis. It is also not known that metal chelate complexes have been selected or synthesized according to this criterion.

The great diagnostic potential has not been recognized that this decomposition of lipophilic heavy-metal complexes in crossing the blood-brain barrier and the retention associated with it opens up a way for the use of these complexes for investigating ion metabolism in the CNS.

All documented efforts exclusively bear on suppressing the decomposition of the utilized tracer as much as possible in a physiological environment or at least delaying it.

And up to today, this knowledge has not been utilized to develop a method that makes possible a direct measurement of the alteration of cation metabolism in vivo.

In a study published in 2004 by Goldschmidt et al., Neuroimage 23(2):638-47, the use of thallium acetate in a high-resolution, non-radioactive method was [described]. This method was primarily conducted in order to make possible a histochemical, high-resolution representation of neuronal activity. The principle for this is that neuronal activity and potassium (thallium) uptake are closely coupled, as is known, and the thallium compound served as a tracer for potassium ions. The basis of the described method is so-called autometallography, which involves a standard detection method for heavy metals. The application of this method is explained in an animal model in which autometallography has been performed as a histochemical method after the tissue has been removed.

The fact that very large amounts of thallium acetate had to be utilized in order to correspond to the sensitivity of the method is a disadvantage with this method. These high thallium doses and the fact that the detection of thallium is made histochemically after removal of tissue make the use of the method impossible in humans. The dose would be deadly even for experimental animals, but the experimental animals were sacrificed as early as 15 minutes after the administration of thallium acetate, and the brains were removed for histochemical investigation.

Apart from the impossibility of working with this method on humans, the use of water-soluble thallium salts still has the disadvantage that the regional thallium distribution is also determined by regional differences in the potassium conductivity of the blood-brain barrier. This limits its use, particularly in the analysis of pathological changes in which the blood-brain barrier is also altered, and also makes it difficult to compare the cellular thallium uptake in different brain regions.

SUMMARY OF THE INVENTION

The object of the present invention is thus to provide a diagnostic substance that makes possible the utilization of free heavy-metal ions for the diagnosis of changes in cation metabolism in the central nervous system without disrupting the blood-brain barrier.

In addition, the object of the present invention is to provide a diagnostic method, in which a broad spectrum of the most varied heavy-metal ions can be utilized as tracers for different cations for the investigation of cation metabolism, also in vitro.

And in addition to this, an object of the present invention is to provide a method for the diagnosis of changes in cation metabolism in the central nervous system, which can be conducted with a substantially lower cost for equipment than in the case of PET, and thus can also be conducted, for example, in the practice of nuclear medicine specialists.

The object is accomplished by providing a diagnostic substance, containing at least one complex of lipophilic anions and metal ions as well as solvents, adjuvants and/or vehicles.

According to the invention, a diagnostic substance is preferred, wherein the lipophilic anions are selected from the group comprising: triethylene tetramine dihydrochloride (TETA), ethyl cysteinate dimer (ECD), methoxyisobutylisonitrile (MIBI), HMPAO (d,l-hexamethylpropylene aminoxime), ethylenediamine N,N,N',N'-tetraacetanilide (EDTAN), dimethyldithiocarbamate (DMC) and diethyldithiocarbamate (DDC) and glycine N,N'-[1,2-ethanediylbis(oxy-2, 1-phenylene)]bis[N-(carboxymethyl)-1,1'-bis[2-(octadecyloxy)ethyl]ester (DP-109) or other anions with corresponding lipophilic properties as well as combinations of the above-named anions.

According to the invention, a diagnostic substance is preferred, wherein the metal ions are selected from the group comprising: thallium isotopes, lead isotopes, cobalt isotopes and manganese isotopes or other metal ions with corresponding properties as well as combinations of the above-named metal ions.

The object of the invention is accomplished in particular by a diagnostic substance, containing at least one complex of lipophilic anions and metal ions, wherein the lipophilic anions are selected from the group comprising: triethylene tetramine dihydrochloride (TETA), ethyl cysteinate dimer (ECD), methoxyisobutylisonitrile (MIBI), HMPAO (d,l-hexamethylpropylene aminoxime), ethylenediamine N,N,N',N'-tetraacetanilide (EDTAN), dimethyldithiocarbamate (DMC) and diethyldithiocarbamate (DDC) and glycine N,N'-[1,2-ethanediylbis(oxy-2,1-phenylene)]bis[N-(carboxymethyl)-1,1'-bis[2-(octadecyloxy)ethyl]ester (DP-109), and wherein the metal ions are selected from the group comprising: thallium isotopes, lead isotopes, cobalt isotopes and manganese isotopes, together with solvents, adjuvants and/or vehicles.

A diagnostic substance is particularly preferred, which contains the following complexed compounds:
Tl-TETA, Tl-ECD, Tl-MIBI, Tl-HMPAO, Tl-EDTAN, Tl-DMC, Tl-DDC, Tl-(DP-109),
Pb-TETA, Pb-ECD, Pb-MIBI, Pb-HMPAO, Pb-EDTAN, Pb-DMC, Pb-DDC, Pb-(DP-109),
Mn-TETA, Mn-ECD, Mn-MIBI, Mn-HMPAO, Mn-EDTAN, Mn-DMC, Mn-DDC, Mn-(DP-109),
Co-TETA, Co-ECD, Co-MIBI, Co-HMPAO, Co-EDTAN, Co-DMC, Co-DDC and/or Co-(DP-109).

In addition, the object of the invention is attained by the use of a diagnostic substance according to the invention for investigating metabolic processes in the brain and/or central nervous system (CNS).

A method is preferred for investigating metabolic processes in the brain and/or CNS, wherein a diagnostic substance according to the invention is administered to a mammal and the distribution of the metal ion contained in the diagnostic substance is measured in tissue.

It is particularly preferred that in the method according to the invention, radioactive metal ions are detected by means of nuclear medicine methods and paramagnetic metal ions are detected by means of nuclear resonance methods.

It is further preferred that in the method according to the invention, the radioactive metal ions are detected by means of SPET or PET methods or a gamma camera.

In particular, it is preferred that in the method according to the invention, paramagnetic metal ions are detected by means of nuclear spin tomography methods.

In addition, it is preferred that the method according to the invention is conducted as a long-term measurement.

BRIEF DESCRIPTION OF THE DRAWINGS

FIG. 2 is a highly resolved image of thallium distribution in the hyperacute stage of cerebral ischemia.

DETAILED DESCRIPTION OF THE INVENTION

Figure 1:
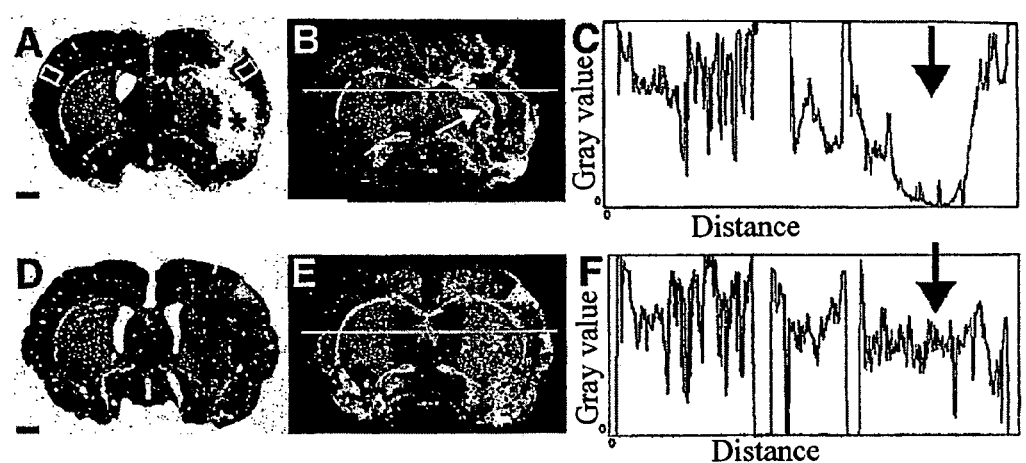
FIG. 1 is an overview of the thallium distribution after Tl-DDC injection in the brain of rat 15 minutes (hyperacute stage, A, B, C) and 7 days (D, E, F) after focal cerebral ischemia.

The object is thus accomplished by providing a diagnostic substance according to the invention and the method according to the invention, whereby the direct investigation of ion metabolism in the brain and/or CNS is made possible.

A diagnostic substance is provided, which contains the selected lipophilic heavy-metal complexes, which are unstable and break down into their ionic components after crossing the blood-brain barrier. Metal ions are released into the extracellular space of the brain by means of this breakdown.

Thus, in one example of embodiment of the invention, the diagnostic substance contains a potassium tracer, namely a lipophilic thallium complex, preferably $^{201}$Tl-DDC. By using this diagnostic substance in the method according to the invention, changes in potassium metabolism, as occur, e.g., in brain infarcts, brain tumors, or degenerative diseases, can be determined in the CNS.

In an analogous way, diagnostic substances according to the invention are provided, which comprise lipophilic lead, cobalt and manganese complexes, which are used in the method according to the invention for investigating changes in CNS metabolism.

In addition, one advantage that the diagnostic-substances according to the invention make possible is the conducting of the method according to the invention as a long-term measurement. In particular, the selection of radioactive metal compounds with relatively long half-life values, the use of which previously was counter-indicated in diagnostic methods of the prior art, can be utilized in the method according to the invention. In the investigation of metabolic processes, along with the instantaneous uptake for determining the current state, the observation of the development of a state as a function of time [is] also of particular interest.

It is thus possible, for example, by means of the method according to the invention as a long-term measurement, to follow the progression of a brain infarct for the first few hours after onset. In this case, for example, the unique possibility of investigating the kinetics of Tl$^+$ uptake and/or Tl$^+$ loss is offered by the use of a lipophilic thallium complex, whereby data of decisive importance for evaluating a therapy can be obtained.

And since a distinction can be made between healthy and damaged brain tissue by means of the method according to the invention, the utilization of the method as a reference investigation for verifying brain death, as is necessary prior to almost every organ donation, is also conceivable.

Another advantage of the method according to the invention is that it can be used also particularly for coma patients. These patients cannot usually be moved to a tomograph.

The complexed compounds contained in the diagnostic substance are produced analogously to methods known in the prior art.

The diagnostic substance according to the invention is produced in a way known in and of itself by suspending or dissolving the complexed compound, optionally in combination with solvents, adjuvants and/or vehicles. Sterilization of the suspension or solution can follow this preparation.

The diagnostic substance is administered parenterally, as is known by a person of average skill in the art.

The metal ions contained in the diagnostic substance are detected in a way known in and of itself in the method according to the invention. The classical methods of SPET or PET or a gamma camera are utilized for the detection of the radioactive isotopes used. All nuclear spin methods known in the prior art can be utilized for the detection of paramagnetic metal ions.

The following example explains the invention.

Example

The distribution of thallium-201 diethyldithiocarbamate ($^{201}$Tl-DDC) in the brain of a rat after injection of a $^{201}$Tl-DDC solution is shown in FIGS. 1 and 2. Thallium is a potassium tracer and can detect changes in potassium metabolism, as occur, e.g., in brain infarcts, brain tumors, or degenerative diseases.

FIG. 1 is an overview of the thallium distribution after Tl-DDC injection in the brain of rat 15 minutes (hyperacute stage, A, B, C) and 7 days (D, E, F) after focal cerebral ischemia. Shown are frontal sections in the plane of the anterior commissure (A, D) and images of the same sections (B, E). The variation in optical density along the white lines in B and E is shown in C and E, respectively.

In the hyperacute stage, an infarct core can be seen (asterisk in A and B, arrow in C), which has a clearly reduced staining intensity but cannot be detected at this early time point with conventional techniques. This region is surrounded by a zone, in which the intensity is higher, but it is still clearly lower than in the undamaged contralateral side.

At the late time point (D, E, F), the differences ipsilateral and contralateral to the occluded vessel are less pronounced (scale bars in A and D: 1 mm).

FIG. 2 shows a highly resolved image of thallium distribution in the hyperacute stage of cerebral ischemia. The rectangles in the overview photomicrograph (A) mark the position of details shown in B, C, E and F. Regions of different staining intensity can be distinguished both in the cerebral cortex (B) and in the caudate-putamen (F) (arrows in B and F). The thallium is taken up essentially by the sodium-potassium pump and transport systems regulated by it and is thus energy-dependent. Cells that can no longer produce the required ATP energy equivalent cannot be stained and cells with reduced pump efficiency can only be stained lightly (e.g., the neuron in D, asterisk). Therefore, thallium cannot be detected in the neurons of the infarct core (C), while on the other hand, the metabolically highly active astrocytes (arrows in C) are intensively stained. These metabolic differences at the cellular level are not detectable with the previous methods, in particular at such early time points after ischemia. The astrocytes also have an increased metabolism in the zone directly adjacent to the core region and thus an intense staining (arrow in D, detail from B). With this technique, metabolic differences can be shown in spatially adjacent cells (astrocyte and neuron in D, arrow). Neurons and neuropil with high metabolic activity also can be detected in the marginal zones of the infarct region both in the cerebral cortex (arrow in E) as well as in the caudate-putamen (asterisk in F). Scale bar in A: 500 μm, in B: 50 μm, in C: 25 μm, in D: 10 μm, in E: 25 μm and in F: 100 μm.

The invention claimed is:

1. A method for investigating changes in cation metabolism in the brain, the method comprising the steps of:
   administering to a mammal a diagnostic substance containing 201Tl-DDC as well as solvents, adjuvants and/or vehicles;
   measuring the distribution of the 201Tl-ion contained in the diagnostic substance in brain tissue using SPET imaging;
   identifying changes in cation metabolism by detecting presence or absence of 201Tl-ions;
   wherein the method is performed in vivo.

2. A method of investigating changes in cation metabolism in the brain for the distinction of healthy and damaged brain tissue over time, the method comprising the steps of:
   administering to a mammal a diagnostic substance containing 201Tl-DDC as well as solvents, adjuvants and/or vehicles,
   measuring and imaging the distribution of the 201Tl-ion contained in the diagnostic substance in tissue using SPET;
   identifying changes in cation metabolism by detecting presence or absence of 201Tl-ions;
   identifying damaged from healthy brain tissue by comparing staining intensities in the imaging,
   wherein the method is performed in vivo.

* * * * *